United States Patent
Ulrici et al.

(10) Patent No.: US 8,750,450 B2
(45) Date of Patent: Jun. 10, 2014

(54) METHOD FOR PRODUCING A DENTAL 3D X-RAY IMAGE, AND X-RAY DEVICE THEREFOR

(75) Inventors: Johannes Ulrici, Darmstadt (DE); Roland Bonk, Eich (DE)

(73) Assignee: Sirona Dental Systems GmbH, Bensheim (DE)

( * ) Notice: Subject to any disclaimer, the term of this patent is extended or adjusted under 35 U.S.C. 154(b) by 331 days.

(21) Appl. No.: 13/055,879

(22) PCT Filed: Jul. 29, 2009

(86) PCT No.: PCT/EP2009/059781
§ 371 (c)(1),
(2), (4) Date: Jan. 31, 2011

(87) PCT Pub. No.: WO2010/012754
PCT Pub. Date: Feb. 4, 2010

(65) Prior Publication Data
US 2011/0129058 A1  Jun. 2, 2011

(30) Foreign Application Priority Data
Jul. 29, 2008 (DE) .......................... 10 2008 035 412

(51) Int. Cl.
*A61B 6/14* (2006.01)
*A61B 5/07* (2006.01)

(52) U.S. Cl.
USPC .................................................. 378/4; 378/38

(58) Field of Classification Search
USPC .............. 378/4, 19, 38, 39, 62, 197
See application file for complete search history.

(56) References Cited

U.S. PATENT DOCUMENTS 4,907,251 A   3/1990  Mork et al. ...................... 378/39
7,787,586 B2 *  8/2010  Yoshimura et al. ............... 378/4
(Continued)

FOREIGN PATENT DOCUMENTS

DE    10 2004 020 370 A1    11/2005
EP       1 815 794 A1        8/2007
(Continued)

OTHER PUBLICATIONS

Machine-generated English translation of a Communication from the German Patent Office dated Aug. 20, 2009, in connection with German Patent Application No. 10 2008 035 412.0.
International Search Report dated Oct. 28, 2009.

*Primary Examiner* — Irakli Kiknadze
(74) *Attorney, Agent, or Firm* — Fitzpatrick, Cella, Harper & Scinto (57) ABSTRACT

In a method for the creation of a dental 3D radiograph of at least a subregion, forming a volume, of an object using an X-ray apparatus, the volume is recorded as a 3D radiograph from a plurality of projected images during a revolution around the object. At least a part of the object is displayed in a graphical representation before the radiograph of the volume is created, the position of the graphical representation relative to the current position of the apparatus and the patient being known. The volume to be radiographed, governed by the positioning of the object relatively to the apparatus and by the choice of the settings data and/or control data, is placed in the graphical representation in an at least approximately correct position, and when there is a change in position and/or size of the volume to be radiographed within the graphical representation, the settings data and/or control data for the creation of the 3D radiograph are defined.

15 Claims, 6 Drawing Sheets

(56) References Cited

U.S. PATENT DOCUMENTS

| | | | |
|---|---|---|---|
| 2004/0081341 A1 | 4/2004 | Cherek et al. | 382/128 |
| 2004/0247069 A1 | 12/2004 | Arai et al. | |
| 2005/0245804 A1 | 11/2005 | Shinohara et al. | 600/407 |
| 2006/0262894 A1* | 11/2006 | Bernhardt et al. | 378/4 |
| 2007/0237287 A1 | 10/2007 | Sukovic et al. | |
| 2009/0052617 A1* | 2/2009 | Sadakane et al. | 378/38 |
| 2009/0310741 A1* | 12/2009 | Borghese et al. | 378/37 |

FOREIGN PATENT DOCUMENTS

| | | |
|---|---|---|
| EP | 2 008 590 A1 | 12/2008 |
| JP | H 2-140150 A | 5/1990 |
| JP | 2004-49615 | 2/2004 |
| JP | 2004-49911 A | 2/2004 |
| JP | 2006-204329 A | 8/2006 |
| JP | 2007-267995 A | 10/2007 |

\* cited by examiner

Fig. 7

METHOD FOR PRODUCING A DENTAL 3D X-RAY IMAGE, AND X-RAY DEVICE THEREFOR

The invention relates to a method for the creation of a dental 3D radiograph of an object and to an X-ray apparatus, by means of which it is possible to reproduce a volume in the form of a 3D radiograph from a plurality of projected images during rotation of the X-ray system around the object.

BACKGROUND OF THE INVENTION

In present-day cone-beam X-ray devices available on the market, a three-dimensional radiograph of a volume is generated for the creation of dental 3D radiographs of the jaw and head region of a patient. The volume is determined as to position and size by the operation of positioning the patient relatively to the apparatus, the selection of the rotational movement of the X-ray emitter and the X-ray detector around the patient, and the adjustment of other variables such as the aperture size, beam geometry, etc.

The problem confronted by the dentist is to preselect the position and/or the size of the volume such that the volume recorded coincides with the region of medical interest. The complexity of this problem increases as the size of the volume to be examined decreases. For this reason, various positioning aids are made available to the operator, these being mostly based on mechanical or optical methods such as monitoring the positioning by means of a light-beam localizer on the patient's head.

DE 10 2004 020 370 A1 discloses an X-ray apparatus in which an optical camera is provided on an X-ray emitter for creating an optical image of the patient's head being X-rayed by said emitter. An optical image can be created at the start of, or during, the rotation of the X-ray emitter around the patient's head in order to facilitate the formation of an association between the radiograph and the visible surface of the object being X-rayed, for diagnostic purposes.

SUMMARY OF THE INVENTION

In the method of the invention for the creation of a 3D radiograph of at least a subregion, forming a volume, of an object by using an X-ray apparatus, including positioning of the object relatively to the apparatus, it being possible to reproduce a volume in the form of a 3D radiograph from a plurality of X-ray projected images during an at least partial revolution of the system, comprising an X-ray emitter and an X-ray detector, around at least a subregion of the object, at least a part of the object being displayed in a graphical representation prior to the creation of the radiograph of the volume, the position of the graphical representation relative to the current position of the apparatus and of the patient being known. The volume to be radiographed, which is governed by the position of the object relative to the apparatus and by the settings data and/or control data, is placed in the graphical representation in an at least approximately correct position.

When the position and/or size of the volume within the graphical representation are changed, the settings data and/or control data for the creation of the 3D radiograph are re-determined or adapted.

The settings data and/or control data define, for example, the position of the axis of rotation of the rotary system comprising the X-ray emitter and the X-ray detector and optionally any variation thereof during rotation, and additional parameters.

The placement in the at least approximately correct position can be achieved, for example, in that during insertion of the volume to be radiographed into the graphical representation, the relative position is determined by comparing the respective position data, that is to say, the position data of the volume to be radiographed and the position data of the graphical representation, and these are appropriately aligned relatively to each other. In doing so, it is sufficient to display the volume to be radiographed as an approximate region when, for example, the recordings are carried out at different imaging angles. Although the at least diagrammatically inserted volume depicts the position and size of the subregion of the object forming a volume, it does not yet have at this point the desired image content that is generated during subsequent rotation.

Advantageously, the graphical representation can be at least part of a surface and/or of a contour of the object. Possible examples of such a graphical representation include an optical image, i.e., for example, a photograph taken in light in the visible range of the spectrum, but also a surface obtained by a scan. In particular, a skull contour may also be considered as a partial image of the object.

It is also possible to compute a three-dimensional contour from a plurality of optical images and to represent the volume within the three-dimensional contour.

Alternatively, the graphical representation may be an existing 3D image or a part thereof. Possible examples of a 3D image include, in particular, a 3D radiograph and a magnetic resonance tomograph (MRT). This existing 3D image may have been created for each patient individually or may have been stored in the form of a standard radiograph capable of being addressed. The use of an already existing 3D image of the object for representing the position of the smaller volume within the object offers the advantage that the user can determine the position more accurately and can select the size of the volume to be radiographed on the basis of information and structures already generated, for example, the shape of nerve canals or roots of teeth.

Furthermore, a plurality of images of the object can be created from different directions and displayed at the same time, the position of the volume being represented in each of these images in the at least approximately correct position.

It is particularly advantageous when, in addition to the representation of the surface and/or the contour of the object, a stored 3D image is displayed at the same time, the volume to be reproduced being displayed both in the representation of the surface and/or contour of the object and in the stored 3D image.

An improved arrangement of the volume is achieved by means of this combination of the external and internal features of the object.

Advantageously, the representation of the surface and/or contour of the object and of the existing 3D image can be automatically aligned to each other in terms of their position, and/or input means can be provided in order to manually align the representation of the surface and/or contour of the object and the existing 3D image to each other in terms of their position.

Advantageously, the graphical representation can comprise an anatomical structure that can be selected from a plurality of predetermined standard anatomical structures or that can be produced from some other existing representation of an anatomical structure. Possible examples of particularly relevant anatomical structures include an alveolar arch, a temporomandibular joint, and/or a wisdom tooth.

Such anatomical structures can also be additionally placed in a different graphical representation, for example, an optical image.

A special advantage is achieved when the position and/or size of the volume can be changed prior to the creation of the 3D radiograph, and when the settings data and/or control data, such as the data involving the positioning of the apparatus and the path of movement followed for creating the projected images for the creation of the volume, are adapted to suit the changed position and/or size of the volume represented diagrammatically.

Advantageously, the diagrammatic volume represented on a display can be moved over the display by means of an input device, and the position data and/or the size of the volume displayed are made known to the X-ray apparatus. The settings data and/or control data for the creation of the image can thus be defined.

It is particularly advantageous when the volume represented on a display and capable of being moved over the display by means of the input device can be moved only so as to maintain an overlap, at least in part, on the anatomical structure shown. As a result, the possibility of an entirely incorrect placement of the volume is eliminated.

A further object of the invention relates to an X-ray system for the creation of dental 3D radiographs, which system comprises a positioning device for positioning the patient in an X-ray apparatus and a system comprising an X-ray emitter and an X-ray detector forming part of the X-ray apparatus and capable of being moved along a path extending around the patient positioned in the positioning device.

Furthermore, a graphical representation of at least a part of the object exists prior to the creation of the 3D radiograph, and display means are provided for the graphical representation. Input means are provided for changing a volume to be radiographed that is displayed on the display means in terms of its position and/or size.

It is thus possible to move the volume represented diagrammatically in the graphical representation across the display unit. Possible examples of the input means include both the control panel of the X-ray apparatus and a display unit that is independent of the X-ray apparatus and that is connected to the X-ray apparatus only for data transfer and that can comprise software for remote control of the X-ray apparatus.

The existing graphical representation present can preferably be a patient-related or standard 3D image of at least one anatomical structure and/or of at least part of a surface and/or of a contour of the object. The 3D image can be, for example, an optical image, a radiograph or a magnetic resonance tomograph.

Furthermore, evaluating means can be provided for determining the settings data and/or control data of the X-ray apparatus, such as the path of movement and the patient's position, from the position and/or size of the volume displayed in the graphical representation. For the creation of the 3D radiograph, the apparatus can be adjusted to the selection area that has been changed via the input means. This means that the position and size of the diagrammatically represented volume determine the settings data and/or control data of the X-ray apparatus for creating the 3D radiograph or the projected radiographs required for this purpose. The settings data and/or control data can also include the patient's position.

Advantageously, an optical camera that is mounted on the X-ray emitter or the X-ray detector or to the side of the X-ray emitter or X-ray detector can be disposed on the system comprising the X-ray emitter and the X-ray detector, while it is possible to provide two or more cameras. The positional relationship between the graphical representation created by the camera and the volume to be radiographed is known, and a graphical representation of the object to be recorded can be produced by means of the camera.

BRIEF DESCRIPTION OF THE DRAWINGS

An exemplary embodiment of the invention is shown in the drawings, in which.

EXEMPLARY EMBODIMENTS OF THE INVENTION

Figure 1:
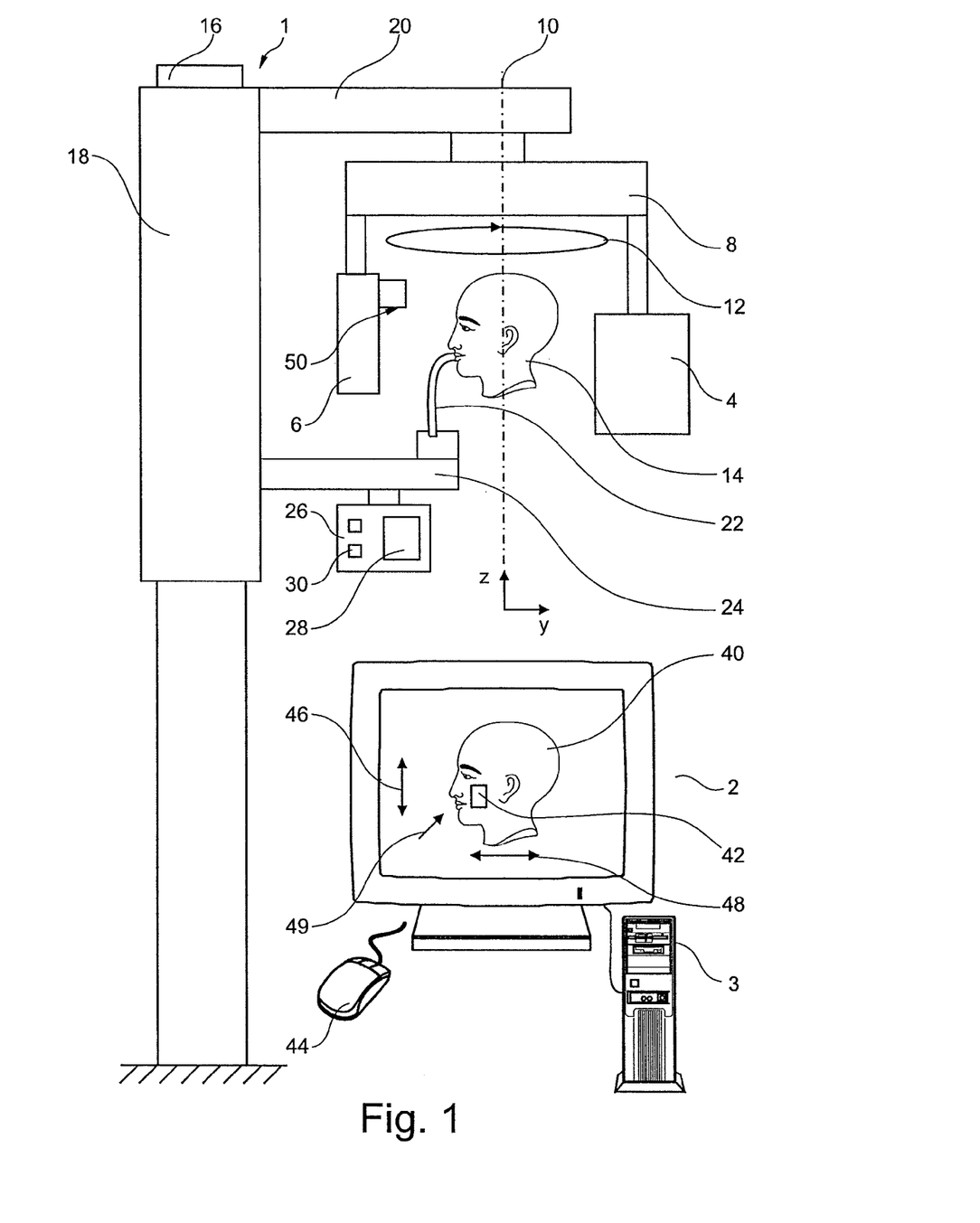
FIG. 1 shows a dental X-ray system for the creation of 3D radiographs in the jaw and head region.

FIG. 1 shows an X-ray system for the creation of 3D radiographs in the jaw and head region, which X-ray system comprises an X-ray apparatus 1 and a display unit 2 that can be part of a PC 3, which is connected to the X-ray apparatus 1 or which can be a part thereof. The X-ray apparatus 1 comprises a system composed of an X-ray emitter 4 and an X-ray detector 6, the X-ray emitter 4 and the X-ray detector 6 being interconnected by means of a supporting beam 8 that can rotate about an axis of rotation 10 around a patient's head 14 serving as the object to be examined. The axis of rotation 10 need not be stationary during rotation of the supporting beam. This axis can, for example, follow an elliptical path.

The supporting beam 8 is mounted for rotation on a slide 18 comprising a radial arm 20 the slide 18 being movable along a column 16 for vertical adjustment. A bite block 22 for positioning the patient's head 14 can further be provided on the vertically adjustable slide 18. The bite block 22 can be provided on a radial arm 24 that can be connected to the slide 18. A control panel 26 comprising a display unit 28 and control buttons 30 can also be provided on the radial arm 24.

For the creation of a graphical representation of the object in the form of optical images, cameras, of which one camera 50 is shown in the figure, are provided on the sensor 6 or to the side of the sensor 6. This is described below in greater detail with reference to FIG. 2.

The optical image 40 of the patient's head 14 created by the camera 50 is shown on the display unit 28 of the control panel 26 or on the external display 2 as a graphical representation in the form of an optical side view—in this case in a recording set-up of the camera 50, at an angle of 90° relative to the angle shown. The image 40 of the patient's head shown on the display 2 comprises a region in which a volume 42 is shown that is to be created by the use of the X-ray system. By default, this volume can assume a standard position and may be adjusted. However, it can alternatively be preselected from a number of standard positions, in which case also it will be possible to subsequently adapt the volume to suit the situation involving the respective patient.

The position of the volume 42 in the displayed image 40 of the patient's head can be altered for this purpose by means of control buttons 30 or input means 44 such as a computer mouse or a light pen or a touch screen, as indicated by the arrows 46, 48. Furthermore, it is possible to change the size of the volume 42, for example by means of a pointer 49 moved by the input means 44.

The transmission of position and size of the displayed volume 42 for the purpose of determining the settings and/or control data of the X-ray system for the creation of the 3D radiograph of the volume 42 can be carried out by evaluating means that are part of the PC 3. The 3D radiograph of the volume 42 can also be produced by means of the PC 3 from different projected images.

Figure 4A:
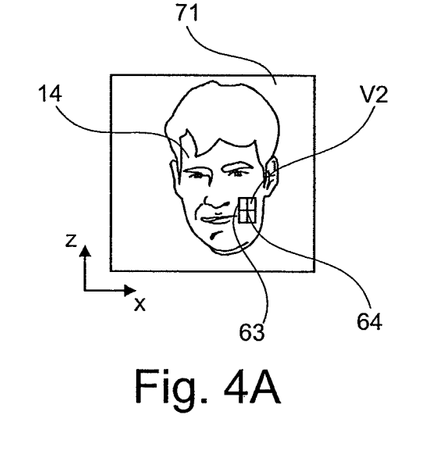
FIGS. 4A, B show displays of the volume recorded as an optical image.
Figure 4B:
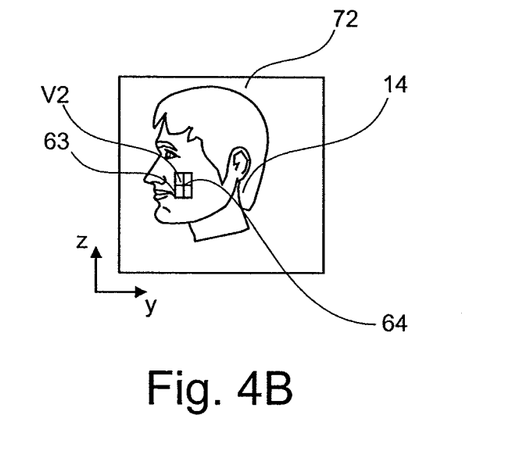
Figure 5:
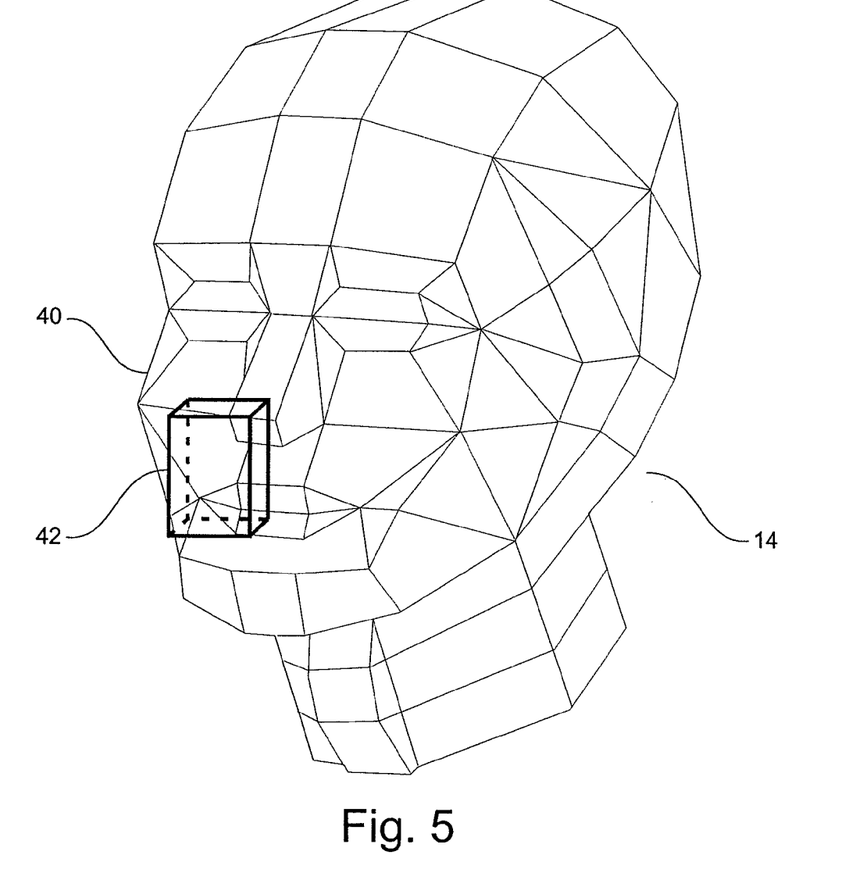
FIG. 5 shows a display of the volume recorded as an optical image in the form of a contour.

The image 40 of the patient's head or a subregion thereof can also be an optical 3D image which includes a plurality of optical images that have been created from different directions and which is represented in the form of a contour 40, for example (FIG. 5). Basically, however, it is sufficient to use two projections from different directions in order to unequivocally determine the position of a smaller volume 42. Thus, instead of a 3D image, it is possible to display a side view of the patient's head and a front view, on which the respective position of the volume is indicated. See FIGS. 4A and 4B.

The image 40 can also be acquired from a scan of the patient's head within the X-ray system, during which measured data are generated initially in the form of individual images from a defined direction. Such scanning methods are well known in the prior art. These measured data can be optionally supplemented by additional measurement recordings from different directions.

Instead of optical images, the object can be scanned, for example mechanically or optically, for which purpose it may be sufficient to define certain measurement points to make it possible to subsequently diagrammatically compute a contour from said measurement points, see FIG. 5.

Figure 2:
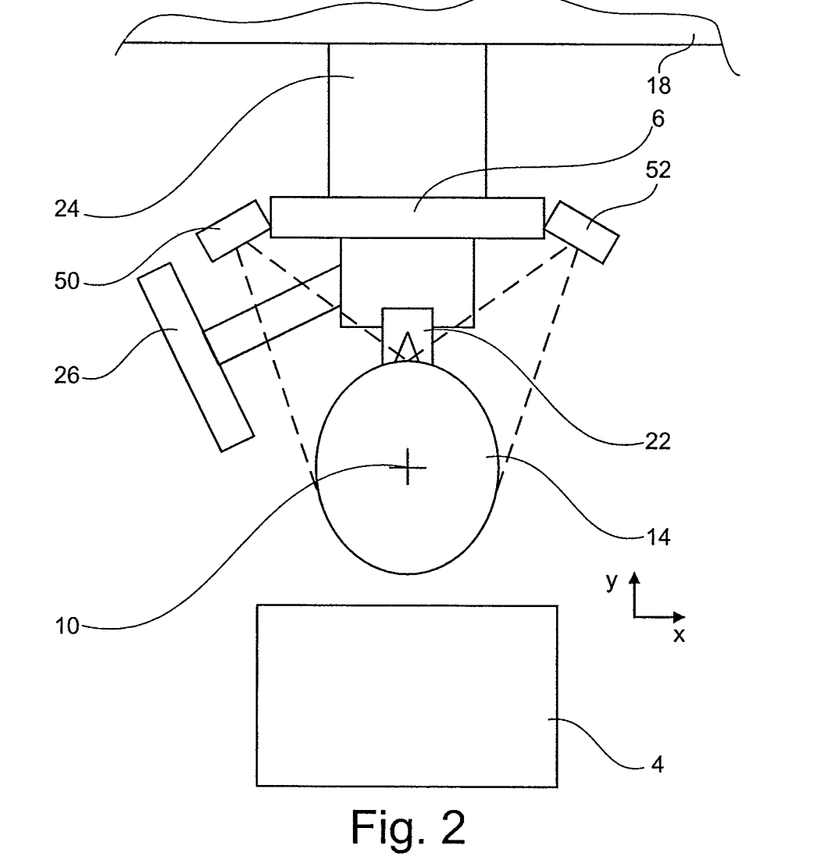
FIG. 2 shows the X-ray system shown in FIG. 1 as a top view.

FIG. 2 is a diagram illustrating the method of creating optical images, starting from the patient's head forming the object to be examined and fixed in position by means of the bite block 22, the radial arm 24, and the slide 18 in the X-ray system. Optical cameras 50, 52 that are directed toward the patient's head 14 from different directions are provided on both sides of the sensor 6. The patient's head 14 can be simultaneously recorded from two directions to give these two recordings, the positions of which in relation to the object to be recorded are known.

If two recordings are inadequate, the sensor 6 can, together with the two cameras 50, 52, be rotated about the axis of rotation 10, as a result of which additional images can be provided from different directions.

An optical 3D scan can also be carried out in this way so that an optical 3D set of measured data of the patient's head can be provided in this way, instead of an optical image.

Figure 3:
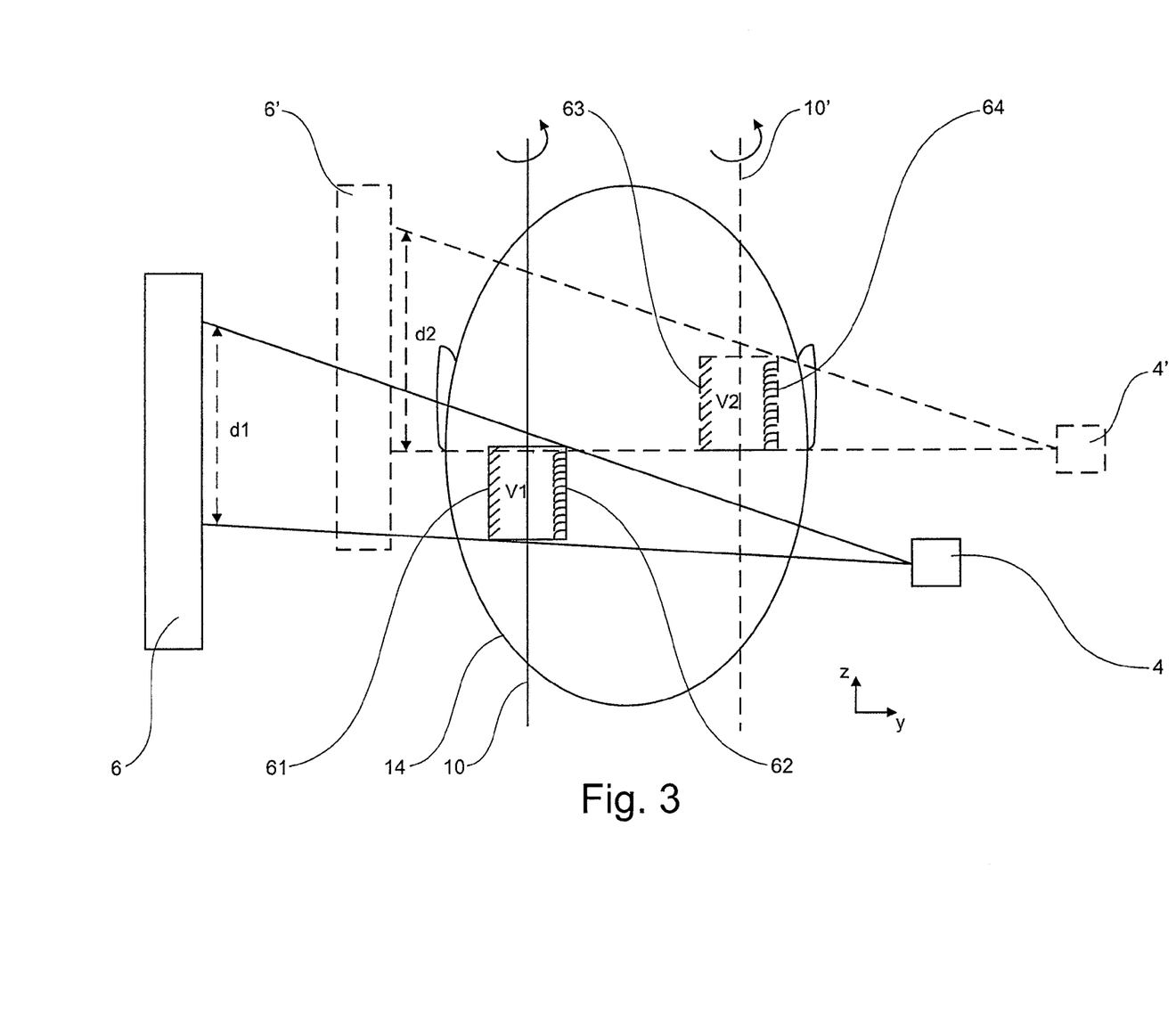
FIG. 3 is a diagrammatic representation of the arrangement of the object in the optical path.

FIG. 3 shows two volumes V1, V2 disposed at different positions in the patient's head 14 displayed as a front view. The position and size of the volume V1, V2 have an effect on the positioning of the patient 14 relatively to the apparatus comprising the emitter 4, 4' and the sensor 6, 6', on the position of the path of movement followed during rotation of the emitter 4, 4' and the sensor 6, 6' about the axis of rotation 10, 10', on the aperture settings for delimiting the cone beam, and optionally on other parameters.

The size d1, d2 of that region of the sensor 6, 6' which is exposed to X-rays can also depend on the position and size of the volume V1, V2.

The boundaries 61, 62 associated with the volume V1 and the boundaries 63, 64 associated with the volume V2 covering the surface of the patient's head 14 are displayed in the optical images relevant to the volume V2 shown in FIGS. 4A and 4B by way of example. Allowance can be made for a conical beam, the aim being to display the volume in its correct size and in a correct position.

FIG. 4A is an optical image 71 in a z-x plane in the form of a full front view of the patient's head 14. FIG. 4B is an optical image 72 in a z-y plane in the form of a side view of the patient's head 14.

A change in the position of the boundaries 63, 64 for the volume V2 alters the size of the volume V2 and the device parameters required for generating the volume V2.

FIG. 5 shows the display of the volume 42 to be radiographed in an optical image 40 of the patient's head 14 in the form of a contour. The volume 42 to be radiographed can be shown as a perspective view.

Figure 6:
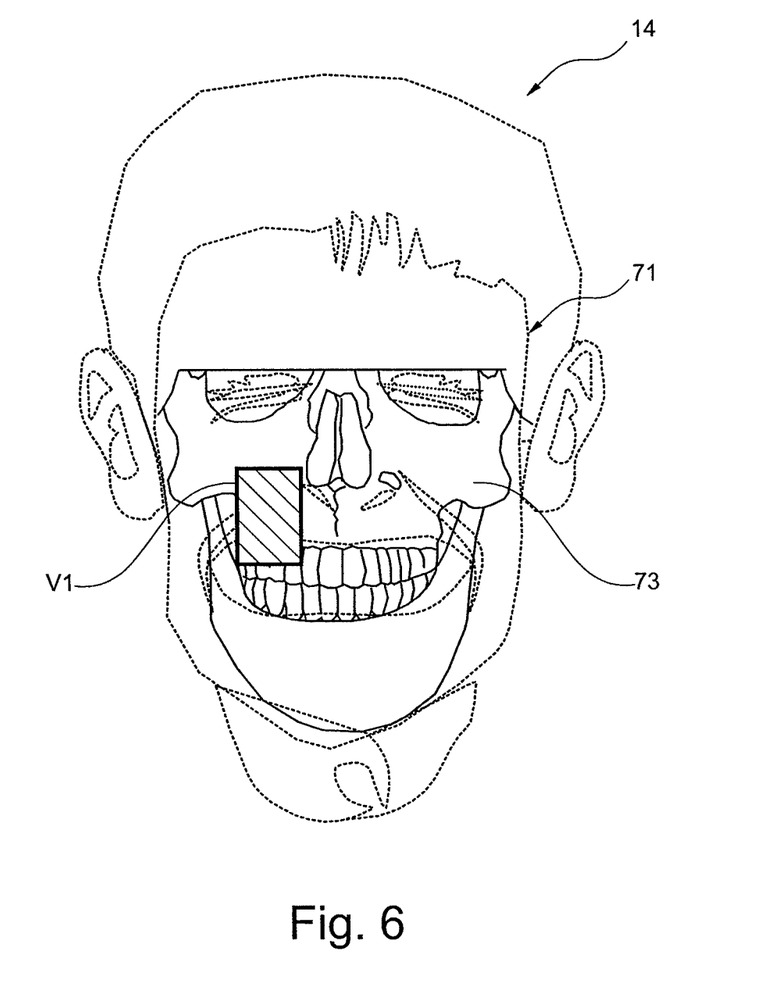
FIG. 6 shows a display of the volume recorded as an optical image together with a concurrently created 3D radiograph.

FIG. 6 shows a stored 3D image 73, in addition to the graphical representation of the image 71 of the object surface shown in FIG. 4A. Instead of a full view of the patient's head, it may suffice to display the lower facial region as a partial image. The image 71 of the object and the 3D radiograph 73 can be positioned relatively to each other by input means, and the volume V1 to be created is displayed in the optical image 71 of the contour of the skull and in the 3D radiograph 73 and can be varied as to position and size.

After the creation of the 3D radiograph of this volume 42, the spatial resolution of the volume V1 is higher than that of the stored 3D radiograph 73 and therefore permits more precise evaluation.

Figure 7:
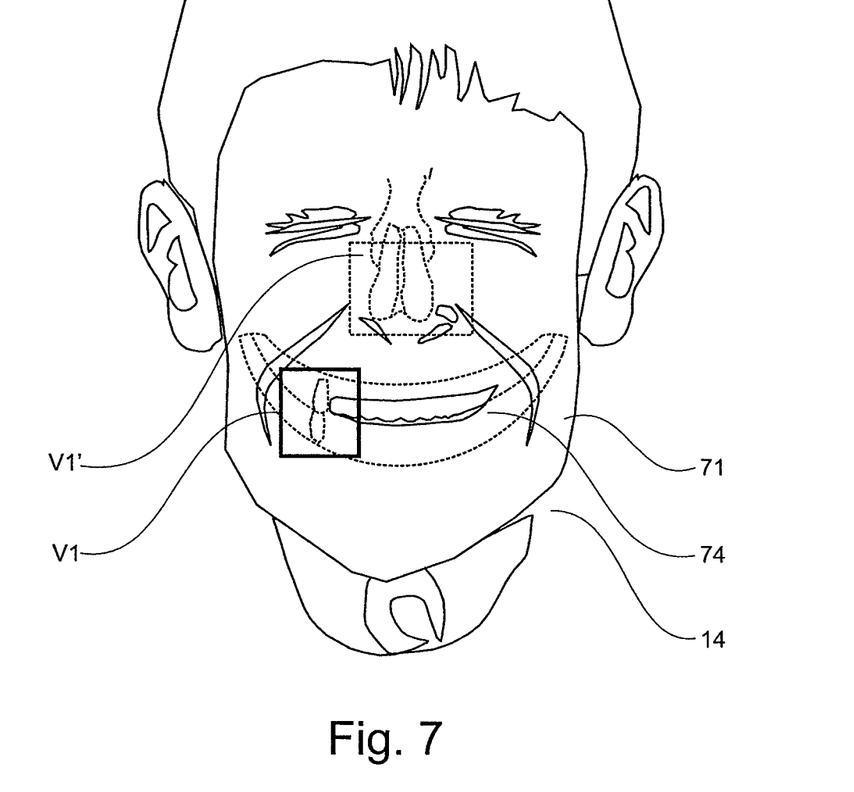
FIG. 7 is a graphical representation of the volume in the form of a contour together with a concurrently shown anatomical structure.

FIG. 7 is a graphical representation of an alveolar arch 74 as an example of an anatomical structure within the optical image 71 of the object, which makes positioning simpler. The alveolar arch 74 can be generated either from a previous image, for example a panoramic tomograph of the patient, or a diagrammatic representation of the anatomical structure can be produced by the dentist himself assessing the shape of the jaw and optionally selecting a suitable diagram from the various diagrams available. It is likewise possible to derive an expected alveolar-arch diagram from the contour of the head.

If there exists a limitation to at least one subregion of the anatomical structure 74 for positioning the volume V1, such positioning can be carried out more reliably, since this structure is then also displayed in the manner proposed by the invention. In this case, it may be advantageous to have limiting values for the minimum overlap ranging, for example, from at least 25% to 50%, depending on the type of image. Placement of the volume V1' outside the anatomical structure 74 would thus be impossible. This requirement could depend on the type of image, that is to say, on a preselection of the type of image, for example, an image of the root of the tooth or of the temporomandibular joint, or the like.

As a general rule, the placement of the volume to be radiographed in a graphical representation of the object, for example in the form of an optical image, or in an already existing 3D-image in an at least approximately correct position requires a type of positional registration that defines the position of the graphical representation relative to the current position of the X-ray apparatus and that of the patient. For example, the data pertaining to the position in which the patient was fixed when creating the graphical representation can be acquired and stored so as to make it possible to compare it with the current position.

In general terms, this means that a comparison of the position of the apparatus relative to the patient in the preceding radiograph with the current position of the apparatus and patient is carried out in order to correctly reproduce the position of the volume to be radiographed in the graphical representation. In the case of the optical images shown in FIG. 2, it is also necessary to produce the optical image if this was not created immediately prior to the creation of the radiograph of the volume.

The invention claimed is:

1. A method for creating a dental three-dimensional (3D) radiograph of at least one subregion, forming a volume, of an object using an X-ray apparatus, the method comprising:
    positioning the object relative to the apparatus;
    creating a 3D radiograph of the volume from a plurality of projected X-ray images during an at least partial revolution of a system of the X-ray apparatus including an X-ray emitter and an X-ray detector around at least a subregion of the object;
    prior to the creating of the radiograph of the volume, displaying at least a part of the object in a graphical representation, a position of the graphical representation relative to a current position of the apparatus and a current position of a patient being predetermined, the volume being governed by the positioning of the object relative to the apparatus and by at least one of settings data and control data, and the volume being shown on the object in the graphical representation and having a position and size that are selectively alterable; and
    automatically adjusting at least one of the settings data and the control data for creating the 3D radiograph, in response to at least one of the position and size of the volume shown on the object within the graphical representation being altered,
    wherein the settings data and the control data define at least one of a position of an axis of rotation of at least part of the X-ray apparatus, a path of movement of at least part of the X-ray apparatus, a position of at least part of the X-ray apparatus, and a position of the object.

2. The method as defined in claim 1, wherein the graphical representation includes at least one of at least part of a surface and a contour of object.

3. The method as defined in claim 2, further comprising:
    calculating a three-dimensional contour from a plurality of optical images; and
    displaying the volume within the three-dimensional contour.

4. The method as defined in claim 2, further comprising:
    creating a plurality of images of the object from a plurality of directions; and
    displaying the plurality of images, wherein at least part of the volume is displayed in each of the images.

5. The method as defined in claim 2, further comprising:
    displaying a stored 3D image in addition to at least one of the surface and the contour of the object, and
    displaying the volume in a representation of at least one of the surface and the contour of the object and in the 3D image.

6. The method as defined in claim 5, further comprising at least one of:
    automatically aligning a position of the representation of at least one of the surface and the contour of the object and a position of the existing 3D image; and
    providing an input unit that controls alignment of the position of the representation of at least one of the surface and the contour of the object and the position of the existing 3D image.

7. The method as defined in claim 1, wherein the graphical representation is an existing 3D image or part of the existing 3D image.

8. The method as defined in claim 1, wherein the graphical representation is selected from a plurality of specified standardized anatomical structures, or the graphical representation includes an anatomical structure produced from an existing graphical representation.

9. The method as defined in claim 8, further comprising:
    displaying the volume on a monitor; and
    displacing the volume displayed on the monitor using an input device of the monitor while maintaining an at least partial overlap on a depicted anatomical structure.

10. The method as defined in claim 1, further comprising modifying at least one of the position and the size of the volume included in the graphical representation prior to creation of the radiograph, and adapting at least one of the position of the patient relative to the apparatus, the settings data, and the control data to at least one of a modified position and a modified size of the volume.

11. The method as defined in claim 10, further comprising displaying the volume on a monitor such that the volume displayed is selectively movable by means of an input device of the monitor; and providing at least one of position data and a size of a volume displayed to the X-ray apparatus.

12. An X-ray system for creating dental three-dimensional (3D) radiographs, the system comprising:
    an X-ray apparatus including a subsystem including an X-ray emitter and an X-ray detector;
    a positioning device that positions a patient with respect to the X-ray apparatus, at least one of the X-ray emitter and the X-ray detector being movable along a path surrounding the patient positioned by the positioning device;
    a display unit that displays a graphical representation of at least part of an object prior to creating at least one 3D radiograph;
    an input unit operable to change a volume to be radiographed that is displayed by the display unit, the volume being shown on the object in the graphical representation displayed by the display unit, and having a position and size that are selectively alterable; and
    a processor arranged to automatically adjust at least one of settings data and control data for creating the at least one 3D radiograph, in response to one of the position and size of the volume shown on the object within the graphical representation being altered,
    wherein the settings data and the control data define at least one of a position of an axis of rotation of at least part of the X-ray apparatus, a path of movement of at least part of the X-ray apparatus, a position of at least part of the X-ray apparatus, and a position of the object.

13. The X-ray system as defined in claim 12, wherein the graphical representation is at least one of a patient-related 3D image of at least one anatomical structure and at least part of at least one of a surface and a contour of object.

14. The X-ray system as defined in claim 12, wherein the processor defines at least one of the settings data and the control data for creating the at least one 3D radiograph from at least one of the position and the size of the volume displayed on the object within the graphical representation.

15. The X-ray system as defined in claim 12, further comprising at least one optical camera disposed on in association with the subsystem including the X-ray emitter and the X-ray detector, a positional relationship between the graphical representation created using the camera and the volume to be radiographed is predetermined.

* * * * *